US009855155B2

(12) United States Patent
Majercak (10) Patent No.: US 9,855,155 B2
(45) Date of Patent: Jan. 2, 2018

(54) ENDOPROSTHESIS ANCHORING AND SEALING (71) Applicant: Cordis Corporation, Fremont, CA (US)

(72) Inventor: David Majercak, Livermore, CA (US)

(73) Assignee: CARDINAL HEALTH SWITZEERLAND 515 GMBH, Bar Zug (CH)

( * ) Notice: Subject to any disclaimer, the term of this patent is extended or adjusted under 35 U.S.C. 154(b) by 0 days.

(21) Appl. No.: 14/316,151

(22) Filed: Jun. 26, 2014

(65) Prior Publication Data

US 2015/0374517 A1   Dec. 31, 2015

(51) Int. Cl.
*A61F 2/852* (2013.01)
*A61F 2/07* (2013.01)
(Continued)

(52) U.S. Cl.
CPC .............. *A61F 2/852* (2013.01); *A61F 2/064* (2013.01); *A61F 2/07* (2013.01); *A61F 2/90* (2013.01);
(Continued)

(58) Field of Classification Search
CPC .... A61F 2/852; A61F 2/90; A61F 2/07; A61F 2/064; A61F 2250/0039; A61F 2002/065; A61F 2220/0016; A61F 2220/0033; A61F 2220/0075; A61F 2230/0069; A61F 2002/067; A61F 2002/061; A61F 2002/075; A61F 2210/0004; A61F 2250/00; A61B 2017/06176

See application file for complete search history.

(56) References Cited

U.S. PATENT DOCUMENTS 3,123,077 A   3/1964   Alcamo
5,776,180 A * 7/1998   Goicoechea .............. A61F 2/07
                                                       606/36
(Continued)

FOREIGN PATENT DOCUMENTS

GB   2472602 A    2/2011
WO   0164137 A1   9/2001
(Continued)

OTHER PUBLICATIONS

International Search Report arid Written Opinion for Application No. PCT/US2015/034314, dated Aug. 19, 2015, 11 pages.
(Continued)

*Primary Examiner* — Julian W Woo
(74) *Attorney, Agent, or Firm* — Khoi Q. Ta (57) ABSTRACT An improved endoprosthesis with an embodiment that includes a generally cylindrical graft portion that extends along a longitudinal axis to define a flow passage and a plurality of stent hoops. The plurality of stent hoops are connected to the graft portion and disposed in a spaced apart relationship along the longitudinal axis. There is at least a first suture disposed along on the outer surface of the main body. The first suture connects at least two of the spaced apart stent hoops together. The first suture also includes unidirectional barbs (or multidirectional barbs) configured to reduce movement of the main body with respect to a direction of blood flow in an artery.

18 Claims, 8 Drawing Sheets (51) Int. Cl.
*A61F 2/90* (2013.01)
*A61F 2/06* (2013.01)
*A61F 2/848* (2013.01)
*A61B 17/06* (2006.01)

(52) U.S. Cl.
CPC ............... *A61B 2017/06176* (2013.01); *A61F 2002/061* (2013.01); *A61F 2002/065* (2013.01); *A61F 2002/067* (2013.01); *A61F 2002/075* (2013.01); *A61F 2002/8483* (2013.01); *A61F 2210/0004* (2013.01); *A61F 2220/0016* (2013.01); *A61F 2220/0033* (2013.01); *A61F 2220/0075* (2013.01); *A61F 2230/0069* (2013.01); *A61F 2250/0039* (2013.01); *A61F 2250/0067* (2013.01)

(56) References Cited

U.S. PATENT DOCUMENTS

| | | | |
|---|---|---|---|
| 5,800,515 A * | 9/1998 | Nadal | A61F 2/07 623/1.15 |
| 6,355,056 B1 * | 3/2002 | Pinheiro | A61F 2/07 623/1.13 |
| 7,226,474 B2 * | 6/2007 | Iancea | A61F 2/07 623/1.13 |
| 8,163,007 B2 * | 4/2012 | Dierking | A61F 2/91 623/1.36 |
| 8,246,652 B2 | 8/2012 | Ruff | |
| 8,715,334 B2 * | 5/2014 | Clerc | A61F 2/848 623/1.14 |
| 2004/0093027 A1 | 5/2004 | Fabisiak et al. | |
| 2006/0178733 A1 * | 8/2006 | Pinchuk | A61F 2/07 623/1.35 |
| 2007/0224237 A1 | 9/2007 | Hwang et al. | |
| 2011/0071614 A1 | 3/2011 | Majercak | |

FOREIGN PATENT DOCUMENTS

| | | |
|---|---|---|
| WO | 2004014236 A1 | 2/2004 |
| WO | 2006028925 A1 | 3/2006 |
| WO | 2007016166 A2 | 2/2007 |
| WO | 2009052188 A1 | 4/2009 |

OTHER PUBLICATIONS

International Preliminary Report on Patentability for Application No. PCT/US2015/034314, dated Dec. 27, 2016, 7 pages.

* cited by examiner

ENDOPROSTHESIS ANCHORING AND SEALING

BACKGROUND

An aneurysm is an abnormal dilation of a layer or layers of an arterial wall, usually caused by a systemic collagen synthetic or structural defect. An abdominal aortic aneurysm is an aneurysm in the abdominal portion of the aorta, usually located in or near one or both of the two iliac arteries or near the renal arteries. The aneurysm often arises in the infrarenal portion of the diseased aorta, for example, below the kidneys. A thoracic aortic aneurysm is an aneurysm in the thoracic portion of the aorta. When left untreated, the aneurysm may rupture, usually causing rapid fatal hemorrhaging.

Aneurysms may be classified or typed by their position as well as by the number of aneurysms in a cluster. Typically, abdominal aortic aneurysms may be classified into five types. A Type I aneurysm is a single dilation located between the renal arteries and the iliac arteries. Typically, in a Type I aneurysm, the aorta is healthy between the renal arteries and the aneurysm and between the aneurysm and the iliac arteries.

A Type II A aneurysm is a single dilation located between the renal arteries and the iliac arteries. In a Type II A aneurysm, the aorta is healthy between the renal arteries and the aneurysm, but not healthy between the aneurysm and the iliac arteries. In other words, the dilation extends to the aortic bifurcation. A Type II B aneurysm may include three dilations. One dilation is located between the renal arteries and the iliac arteries. Like a Type II A aneurysm, the aorta is healthy between the aneurysm and the renal arteries, but not healthy between the aneurysm and the iliac arteries. The other two dilations are located in the iliac arteries between the aortic bifurcation and the bifurcations between the external iliacs and the internal iliacs. The iliac arteries are healthy between the iliac bifurcation and the aneurysms. A Type II C aneurysm also may include three dilations. However, in a Type II C aneurysm, the dilations in the iliac arteries extend to the iliac bifurcation.

A Type III aneurysm is a single dilation located between the renal arteries and the iliac arteries. In a Type III aneurysm, the aorta is not healthy between the renal arteries and the aneurysm. In other words, the dilation extends to the renal arteries.

A ruptured abdominal aortic aneurysm is presently the thirteenth leading cause of death in the United States. The routine management of abdominal aortic aneurysms has been surgical bypass, with the placement of a graft in the involved or dilated segment. Although resection with a synthetic graft via a transperitoneal or retroperitoneal procedure has been the standard treatment, it is associated with significant risk. For example, complications include perioperative myocardial ischemia, renal failure, erectile impotence, intestinal ischemia, infection, lower limb ischemia, spinal cord injury with paralysis, aorta-enteric fistula, and death. Surgical treatment of abdominal aortic aneurysms is associated with an overall mortality rate of five percent in asymptomatic patients, sixteen to nineteen percent in symptomatic patients, and is as high as fifty percent in patients with ruptured abdominal aortic aneurysms.

Disadvantages associated with conventional surgery, in addition to the high mortality rate, include an extended recovery period associated with the large surgical incision and the opening of the abdominal cavity, difficulties in suturing the graft to the aorta, the loss of the existing thrombosis to support and reinforce the graft, the unsuitability of the surgery for many patients having abdominal aortic aneurysms, and the problems associated with performing the surgery on an emergency basis after the aneurysm has ruptured. Further, the typical recovery period is from one to two weeks in the hospital and a convalescence period, at home, ranging from two to three months or more, if complications ensue. Since many patients having abdominal aortic aneurysms have other chronic illnesses, such as heart, lung, liver and/or kidney disease, coupled with the fact that many of these patients are older, they are less than ideal candidates for surgery.

The occurrence of aneurysms is not confined to the abdominal region. While abdominal aortic aneurysms are generally the most common, aneurysms in other regions of the aorta or one of its branches are possible. For example, aneurysms may occur in the thoracic aorta. As is the case with abdominal aortic aneurysms, the widely accepted approach to treating an aneurysm in the thoracic aorta is surgical repair, involving replacing the aneurysmal segment with a prosthetic device. This surgery, as described above, is a major undertaking, with associated high risks and with significant mortality and morbidity.

Over the past five years, there has been a great deal of research directed at developing less invasive, endovascular, i.e., catheter directed, techniques for the treatment of aneurysms, specifically abdominal aortic aneurysms. This has been facilitated by the development of vascular stents, which can and have been used in conjunction with standard or thin-wall graft material in order to create a stent-graft or endograft. The potential advantages of less invasive treatments have included reduced surgical morbidity and mortality along with shorter hospital and intensive care unit stays.

Stent-grafts or endoprostheses are now Food and Drug Administration (FDA) approved and commercially available. Their delivery procedure typically involves advanced angiographic techniques performed through vascular accesses gained via surgical cut down of a remote artery, which may include the common femoral or brachial arteries. Over a guidewire, the appropriate size introducer will be placed. The catheter and guidewire are passed through the aneurysm. Through the introducer, the stent-graft will be advanced to the appropriate position. Typical deployment of the stent-graft device requires withdrawal of an outer sheath while maintaining the position of the stent-graft with an inner-stabilizing device. Most stent-grafts are self-expanding; however, an additional angioplasty procedure, e.g., balloon angioplasty, may be required to secure the position of the stent-graft. Following the placement of the stent-graft, standard angiographic views may be obtained.

Due to the large diameter of the above-described devices, typically greater than twenty French (3F=1 mm), arteriotomy closure typically requires open surgical repair. Some procedures may require additional surgical techniques, such as hypogastric artery embolization, vessel ligation, or surgical bypass in order to adequately treat the aneurysm or to maintain blood flow to both lower extremities. Likewise, some procedures will require additional advanced catheter directed techniques, such as angioplasty, stent placement and embolization, in order to successfully exclude the aneurysm and efficiently manage leaks.

While the above-described endoprostheses represent a significant improvement over conventional surgical techniques, there is a need to improve the endoprostheses, their method of use and their applicability to varied biological conditions. Accordingly, in order to provide a safe and effective alternate means for treating aneurysms, including abdominal aortic aneurysms and thoracic aortic aneurysms, a number of difficulties associated with currently known endoprostheses and their delivery systems must be overcome. One concern with the use of endoprostheses is the prevention of endo-leaks and the disruption of the normal fluid dynamics of the vasculature. Devices using any technology should preferably be simple to position and reposition as necessary, should preferably provide an acute, fluid tight seal, and should preferably be anchored to prevent migration without interfering with normal blood flow in both the aneurysmal vessel as well as branching vessels. In addition, devices using the technology should preferably be able to be anchored, sealed, and maintained in bifurcated vessels, tortuous vessels, highly angulated vessels, partially diseased vessels, calcified vessels, odd shaped vessels, short vessels, and long vessels. In order to accomplish this, the endoprostheses should preferably be highly durable, extendable and re-configurable while maintaining acute and long-term fluid tight seals and anchoring positions.

The endoprostheses should also preferably be able to be delivered percutaneously utilizing catheters, guidewires and other devices which substantially eliminate the need for open surgical intervention. Accordingly, the diameter of the endoprostheses in the catheter is an important factor. This is especially true for aneurysms in the larger vessels, such as the thoracic aorta. In addition, the endoprostheses should preferably be percutaneously delivered and deployed such that surgical cut down is unnecessary.

The repair device should also be able to maintain fluid tight seals, especially in devices forming a number of independent interlocking or overlapping components.

SUMMARY OF THE DISCLOSURE

Accordingly, I have devised an improved endoprosthesis that is believed to be heretofore not available in the prior art. In particular, my improvement is an endoprosthesis for repair of aneurysm. The endoprosthesis can also be used in an artery that has an arterial bifurcation for blood to flow downstream from the artery to the bifurcation. The endoprosthesis may include a main body along with first and second tubular extensions. The main body of the endoprosthesis is configured to be placed in an artery upstream of the arterial bifurcation. The main body has a distal end with an anchor portion connected to a fabric portion of the main body. The fabric has inner and outer surfaces and is connected to a first plurality of spaced apart stent hoops. The main body extends from the distal end along a longitudinal axis into two tubular flow passages or legs. Each of the legs including respective second and third plurality of spaced apart stent hoops connected to the fabric portion of each leg. The first tubular extension is configured for insertion into one of the two legs. The second tubular extension is configured for insertion into the other of the two legs, each of the first and second tubular extensions having an outer surface and an inner surface. In the endoprosthesis, there is at least a first suture disposed along on the outer surface of the main body. The first suture connects at least two of the spaced apart stent hoops on the main body together. The first suture may include unidirectional barbs configured to reduce movement of the main body with respect to the artery in the direction of blood flow when the endoprosthesis is implanted into the artery.

I have also devised another endoprosthesis that includes a generally cylindrical graft portion that extends along a longitudinal axis to define a flow passage and a plurality of stent hoops. The plurality of stent hoops are connected to the graft portion and disposed in a spaced apart relationship along the longitudinal axis. There is at least a first suture disposed along on the outer surface of the main body. The first suture connects at least two of the spaced apart stent hoops together. The first suture also includes unidirectional barbs configured to reduce movement of the main body with respect to a direction of blood flow in an artery.

I have further devised another endoprosthesis that includes a generally cylindrical graft portion, a plurality of stent hoops and at least a suture. The generally cylindrical graft portion extends along a longitudinal axis to define a flow passage from a first end to a second end. The plurality of stent hoops are connected to the graft portion and disposed in a spaced apart relationship along the longitudinal axis. Each stent hoop circumscribes about the longitudinal axis in a sinusoidal path about the longitudinal axis that presents apices spaced apart about the longitudinal axis. The at least one suture circumscribes the longitudinal axis and connects to the apices of the stent hoop. Such suture is configured to include barbs in opposing configuration between at least two apices.

In addition to the embodiments described above, other features recited below can be utilized in conjunction therewith. For example, the first suture comprises a plurality of sutures connected to the anchor portion and at least two spaced apart stent hoops; the first suture comprise a plurality of sutures connected to an apex of one stent hoop to an apex of another stent hoop; the first suture comprises a bioresorbable material; the first suture comprises a non-bioresorbable material; the first suture comprises a shape memory material. The endoprosthesis may also include suture knots extending through the graft portion to secure the at least a first suture to the graft portion and the stent hoop; the knots are located proximate respective apices that are defined by a sinusoidal structure of the stent hoop; the spaced apart stent hoops are disposed on the inner surface of the graft portion; the endoprosthesis may include at least a second suture disposed along the outer surface of a distal end of at least one of the tubular extensions so that unidirectional barbs disposed on the at least second suture prevents movement of the at least one tubular extension relative to the respective legs of the main body; the endoprosthesis may include at least a third suture disposed along the outer surface of a proximal end of at least one of the tubular extensions so that unidirectional barbs disposed on the at least second suture; the endoprosthesis may include at least a fourth suture disposed about the circumference of the outer surface of the graft material proximate a junction between the anchor portion and the graft portion of the main body, the fourth suture comprising a section having barbs oriented in a first direction and another section having barbs oriented in a second direction generally opposite the first direction; the first suture includes a bioactive agent dispersed in the first suture to aid in a healing response; the barbs include a continuous helical protrusion; the barbs include projections extending away from the suture; the barbs include projections extending away from the suture at an angle relative to the suture; the barbs include undulations formed as part of the suture.

BRIEF DESCRIPTION OF THE FIGURES

The foregoing and other features and advantages of the invention will be apparent from the following, more particular description of preferred embodiments of the invention, as illustrated in the accompanying drawings.

The accompanying drawings, which are incorporated herein and constitute part of this specification, illustrate presently preferred embodiments of the invention, and, together with the general description given above and the detailed description given below, serve to explain features of the invention (wherein like numerals represent like elements).

MODES OF CARRYING OUT THE INVENTION

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±10% of the recited value, e.g. "about 90%" may refer to the range of values from 81% to 99%. In addition, as used herein, the terms "patient," "host," "user," and "subject" refer to any human or animal subject and are not intended to limit the systems or methods to human use, although use of the subject invention in a human patient represents a preferred embodiment. The uses of the terms "cranial" or "caudal" are in this application are used to indicate a relative position or direction with respect to the person receiving the implant. As applied to "cranial," the term indicates a position or direction closer to the heart, while the term "caudal" indicates a position or direction further away from the heart of such a subject.

Aneurysm repair devices make take on a wide variety of configurations. Aneurysm repair devices may include one element configurations or multiple element or modular element configurations. The secondary sealing mechanisms of the present invention may be utilized with many types of aneurysm repair devices that rely on a primary seal of fabric mesh against the vessel wall. While Abdominal Aortic Aneurysm (AAA) repair devices are used as specific examples, it is contemplated that this unique sealing mechanism can be used with many other types of devices at various other locations.

Figure 1A:
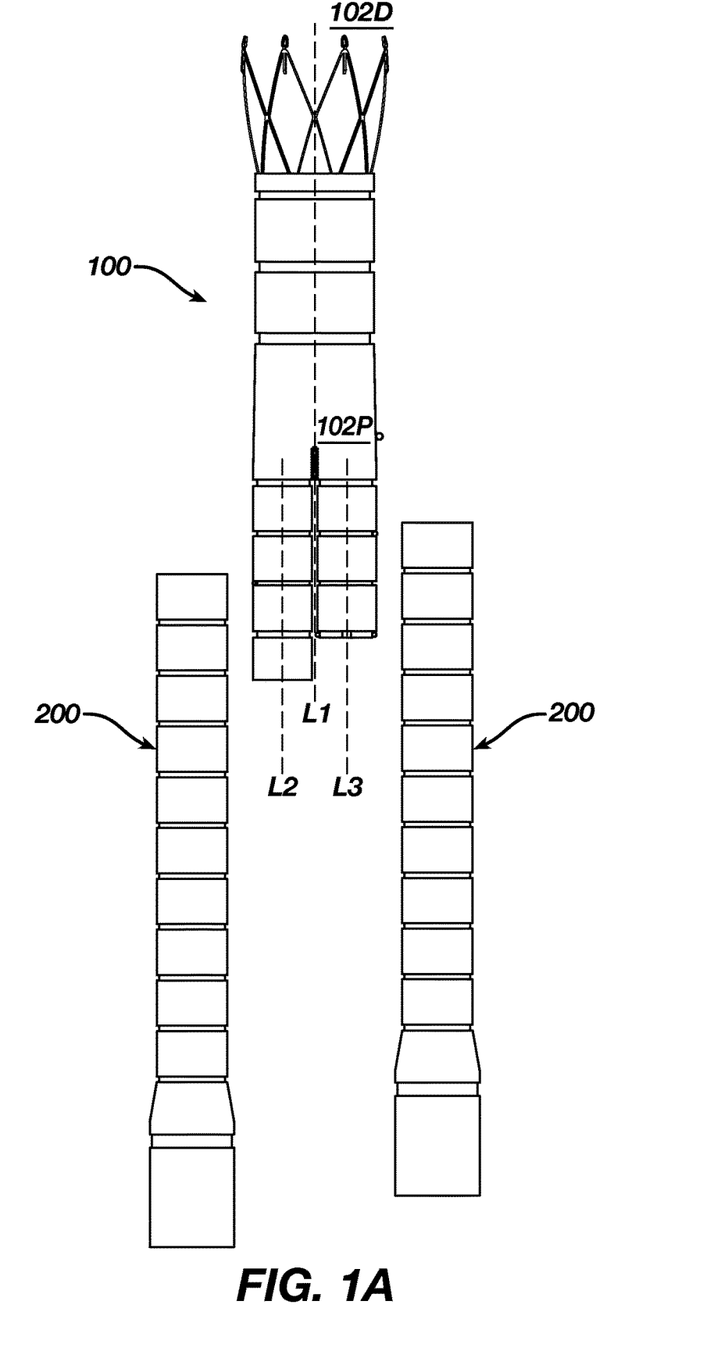
FIG. 1A illustrates the modular endoprosthesis in schematic form having a main body that bifurcates into two legs as well as respective extensions of different lengths for each of the two legs of the main body.

Referring to FIG. 1A, there is illustrated an exemplary anchoring and sealing system of a modular aneurysm repair device. The anchoring and sealing system may include a main portion 100 with two modular extensions 200. The main portion 100 includes trunk section 102 that extends from a cranial portion 102D toward a caudal portion 102P proximate a bifurcated section, which includes two legs, each defining respective longitudinal axes L2 and L3. The combination of the graft material and the underlying scaffold structures creates a blood carrying conduit for insertion into a vessel. The graft material may be attached to the underlying scaffold structures via any suitable means. In the exemplary embodiment set forth herein, the graft material may be attached to portions of the underlying scaffold structures by sutures. As is explained in detail subsequently, the types of sutures utilized as well as the type of stitches may be varied depending on their location and function. The sutures may include any suitable biocompatible material that is preferably highly durable and wear resistant. Graft material 110, described in detail below in FIG. 1B, and may be affixed to at least a portion of the trunk section 102 and to both of the legs 106 and 108.

Figure 1B:
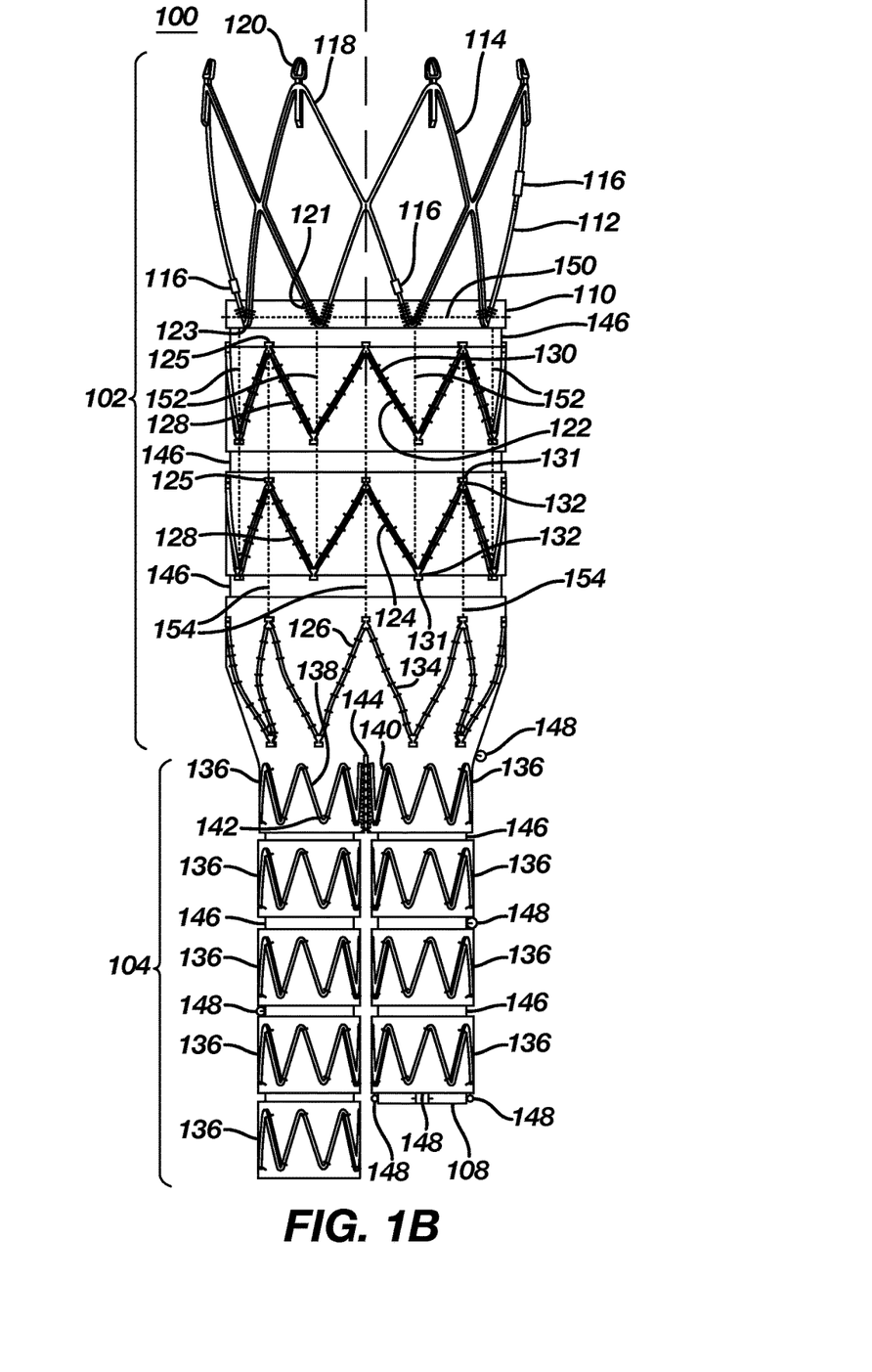
FIG. 1B is a diagrammatic representation of the exemplary anchoring and sealing prosthesis in accordance with one embodiment of the present invention.

As shown in FIG. 1B, the underlying scaffold structures of the trunk section 102 may include a number of substantially tubular stent structures, which may be formed from any number of suitable materials. The upper or cranial end of the trunk section 102 may include a first stent hoop 112 having a diamond shaped configuration formed from a plurality of struts 114. Marker bands 116 formed from a highly radiopaque material such as tantalum may be positioned at various locations on the struts 114 for imaging purposes during device implantation. In other words, the markers 116 may help the physician to visualize the device under radio fluoroscopy. At the upper apex 118 of each diamond cell is an eyelet and barb structure 120. The eyelet portion is utilized in conjunction with a delivery system while the barb portion is utilized to affix the anchoring and sealing component 100 in the vessel into which it is placed.

As may be readily seen from FIG. 1B, the upper portion of the first stent hoop 112 is not covered with graft material 110. This portion is not covered so that it does not interfere with or otherwise impede blood flow to or from cross or branch arteries, for example, the renal arteries. The lower portion of the first stent hoop 112; however, is covered by graft material 110. Sutures 121 are utilized to secure the graft material to the lower or caudal apexes 123 of the first stent hoop 112. To ensure securement of the main portion to the artery with little to no rotational movement about longitudinal axis L1, suture 150 can be provided with barbs. Details of this securement mechanism can be seen in greater details in FIG. 1C.

Figure 1C:
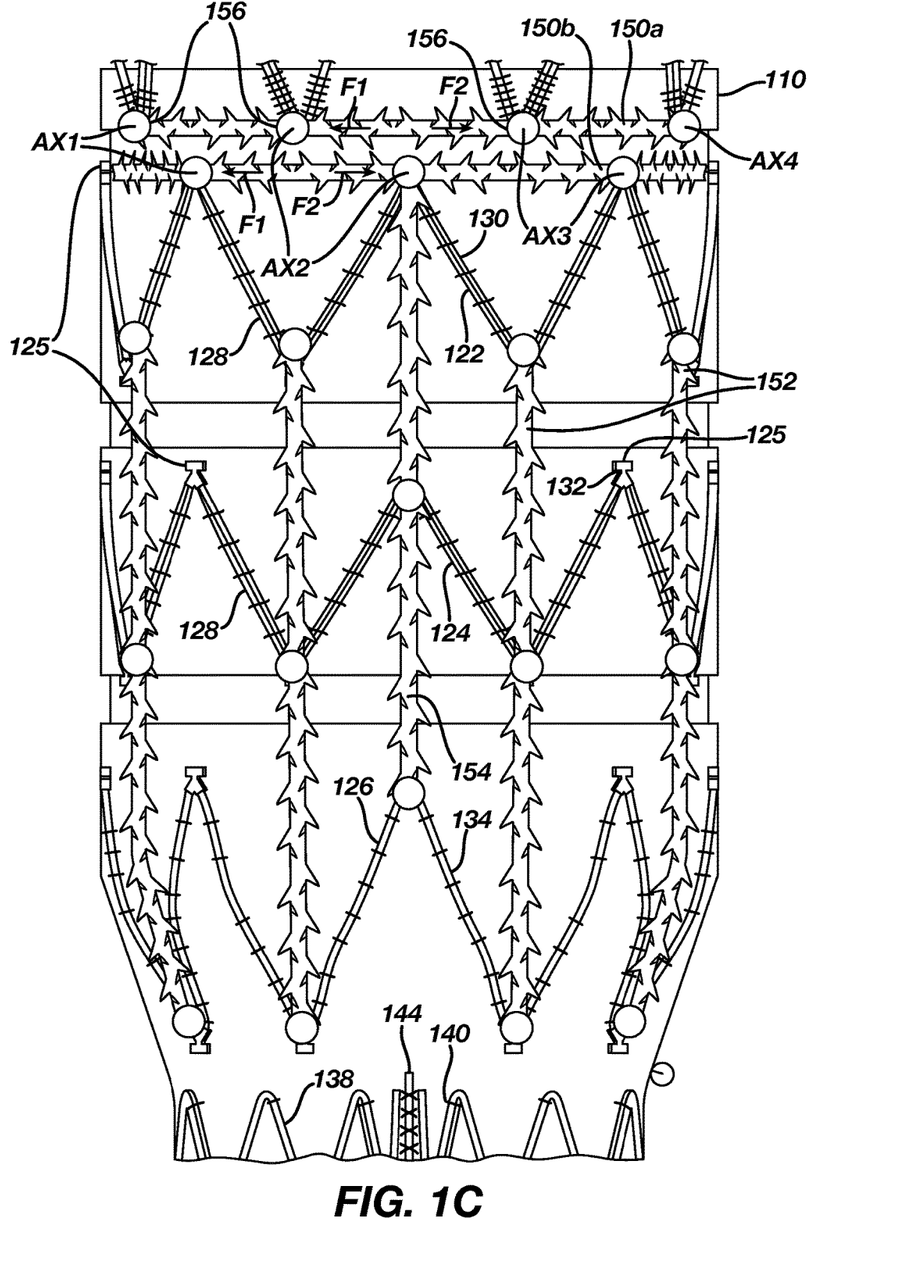
FIG. 1C is a close-up illustration of the main body of FIG. 1A but without the anchor section to illustrate the exemplary sutures that may be utilized.

In FIG. 1C, the suture 150 can be configured to circumscribe the outer surface of the graft material 100 with knots 156 to secure the suture 150 to the apices of the anchoring stent 112 (not shown for clarity). The suture 150 is preferably configured to include barbs that are in opposing directions about the longitudinal axis L1 such that between the apices (AX1, AX2, AX3, AX4 . . . AXn) the barbs on the suture 150a or 150b are situated in an opposing configuration (shown by opposing directional arrows F1 and F2 which represent the resistance to any force applied in opposition to these directional arrows). In this opposing configuration, the opposing barbs on suture 150a for example, prevent the apices AX2 and AX3 from approaching each other. By preventing the apices AX1, AX2, AX3, AX4 . . . AXn (where n=integer) from approaching each other (and thereby moving the endoprosthesis towards a collapsed or unexpanded configuration), the endoprosthesis is maintained at its optimum diameter while in the blood vessel. The benefits of such configuration of the barbs in suture 150a and 150b are that the endoprosthesis is virtually prevented from rotating with respect to the longitudinal axis L1 and leaks of blood flow past the endoprosthesis proximate the sutures 150a or 150a are virtually prevented if not eliminated. While sutures 150a and 150b are shown at the cranial portion of the endoprosthesis, such sutures can be utilized at any portion including the extensions 200 where these benefits are desired.

Referring back to FIG. 1B, the lower or caudal portion of the trunk section 102 may include three individual stent hoops 122, 124 and 126. Stent hoops 122 and 124 are identical in design, with each forming a single row of struts 128 arranged in a substantially zigzag configuration. Sutures 130 are utilized to attach the graft material 110 to each of the stent hoops 122 and 124. In addition, each stent hoop 122 and 124 may include a suture locking mechanism 131 on at least one upper and lower apex 132. These suture locking mechanisms 131 allow for special suture knots to secure the graft material 110 to the stent hoops 122 and 124. It has been determined that these locations are subject to wear due to high biological forces and thus additional securing mechanisms are utilized to prevent separation of the graft material 110. Stent hoop 126 is identical to stent hoops 122 and 124 with one exception. Specifically, the struts 134 forming this third stent hoop 126 are tapered inward in the circumferential direction thereby causing the diameter of the lower portion of the trunk section 102 to decrease where it connects to the bifurcated section 104. As with the other two stent hoops 122 and 124, stent hoop 126 also may include suture locking mechanisms 131 on at least one upper and lower apex 132.

As described above, the bifurcated section 104 includes two legs 106 and 108. As may be readily seen from FIG. 1B, leg 106 is longer than leg 108. This configuration eases deliverability. Each leg 106 and 108 is otherwise identical, and may include a plurality of individual, substantially tubular stent hoops 136. Each stent hoop 136 may include a single row of struts 138 arranged in a substantially zigzag configuration. Sutures 140 are utilized to secure the graft material 110 to the stent hoops 136. These sutures 140, unlike sutures 130 and 121 are only utilized to secure the graft material 110 proximate the apexes 142 of the stent hoops 136 rather than along the entire length of a strut. Each leg 106 and 108 is free to move independently of each other; however, proximate the junction with the trunk section 102, the graft material 110 of each leg 106 and 108 is stitched together with sutures 144. This is done to prevent tearing of the graft material 110 if and when the legs 106 and 108 move.

It is worthwhile to note that the graft material 110 covering the anchoring and sealing component 100 may include crimped sections 146 between the various underlying scaffold elements. These crimped sections increase the flexibility of the entire device.

In use, the anchoring and sealing component 100 is percutaneously positioned in a blood vessel with one or more aneurysms. It is anchored in healthy tissue above the aneurysm and serves as the first conduit to bypass the diseased section of the artery. Additional stent-graft components or endovascular grafts attach to the legs 106 and 108 to extend the bypass to healthy tissue beyond the aneurysm. The system is designed as a modular system so that as many extensions as necessary may be utilized. Essentially, the additional or modular components overlap and form an interference fit. This particular exemplary embodiment having two legs is specifically designed for branching into two vessels, for example, from the abdominal aortic artery to the iliac arteries. However, other similar modular components may be utilized in any other suitable artery.

To aid in the correct positioning of the anchoring and sealing component 100, additional markers 148 are affixed to the device in various locations. The additional markers 148 may be formed out of any suitable, highly radiopaque material such as tantalum. The additional markers 148 may be attached to either or both of the underlying stent structures and the graft material by any suitable means, including stitches and glue. In the exemplary embodiment, the additional markers 148 are attached to the graft material.

FIG. 1B is a close-up view of the main body 102 of the endoprosthesis without the anchor section 116. In particular, main body 102 is configured to be placed in an artery (e.g., abdominal artery) upstream of the arterial bifurcation. As shown previously in FIG. 1A, the main body 102 has a caudal end 102d with an anchor portion 116 connected to a fabric portion or graft material 210 of the main body. The fabric portion 210 has inner and outer surfaces. The fabric portion is connected to a first plurality of spaced apart stent hoops 122, 124, 126 and so on. The main body extends from the caudal end 102d along a longitudinal axis L1 into two tubular flow passages or legs 106 and 108. As noted earlier, each of the legs includes respective second and third plurality of spaced apart stent hoops 136 (FIG. 1B) connected to the fabric portion of each leg. In this embodiment, there is provided a first suture 152 that connects the anchor portion and at least two spaced apart stent hoops. In a preferred embodiment, the first suture 152 includes from four to eight of the first suture 152 depending on the number of apices 125 for the anchor portion and the stent hoops 122, 124, or 126. In an alternative embodiment, the first suture may include a plurality of sutures 154 connected to an apex 125 of one stent hoop 122 to an apex of another stent hoop 124.

Of note is first suture 152 or 154 disposed along on the outer surface of the main body with a physical configuration to allow the main body to remain in place once deployed in the blood vessel despite the hydrodynamic forces of blood flow impinging upon the endoprosthesis. Here, the first suture 152 or 154 connects at least two of the spaced apart stent hoops 122 and 124 on the main body together with unidirectional barbs provided on the suture 152 or 154 to reduce movement of the main body with respect to the artery in the direction of blood flow (i.e., movement along longitudinal axis from the caudal end to the cranial bifurcated portion).

It is noted that in the application of the endoprosthesis for aneurysms, the first suture 152 or 154 may be a non-bioresorbable material. In other applications, the first suture 150, second suture 152, or third suture 154 may be formed from a bioresorbable material. Suitable biodegradable materials may include polymers such as polylactic acid (i.e., PLA), polyglycolic acid (i.e., PGA), polydioxanone (i.e., PDS), polyhydroxybutyrate (i.e., PHB), polyhydroxyvalerate (i.e., PHV), and copolymers or a combination of PHB and PHV (available commercially as Biopol®), polycaprolactone (available as Capronor®), polyanhydrides (aliphatic polyanhydrides in the back bone or side chains or aromatic polyanhydrides with benzene in the side chain), polyorthoesters, polyaminoacids (e.g., poly-L-lysine, polyglutamic acid), pseudo-polyaminoacids (e.g., with back bone of polyaminoacids altered), polycyanocrylates, or polyphosphazenes. As used herein, the term "bio-resorbable" includes a suitable biocompatible material, mixture of materials or partial components of materials being degraded into other generally non-toxic materials by an agent present in biological tissue (i.e., being bio-degradable via a suitable mechanism, such as, for example, hydrolysis) or being removed by cellular activity (i.e., bioresorption, bioabsorption, or bio-resorbable), by bulk or surface degradation (i.e., bioerosion such as, for example, by utilizing a water insoluble polymer that is soluble in water upon contact with biological tissue or fluid), or a combination of one or more of the bio-degradable, bio-erodable, or bio-resorbable material noted above. In yet other applications, the suture 152 or 154 may be a shape memory material such as shape memory metal or polymers.

To secure the suture 152 or 154 to the main body of the prosthesis, suture knots 156, shown here in FIG. 1C, are provided so as to extend through the graft portion or graft material to secure at least the first suture 152 or 154 to the graft material and the stent hoop (122, 124 or 126). Specifically, the knots 156 are located proximate respective apices 125 that are defined by a sinusoidal (i.e., zig-zag like waveform that circumscribes the longitudinal axis to present spaced apart apices about the longitudinal axis L-L) structure of the stent hoop 122, 124, or 126. In the preferred embodiments, the spaced apart stent hoops 122, 124, and 126 are disposed on the inner (i.e., inside) surface of the graft material so that the stent hoops are not in direct contact with the blood vessel tissue.

Figure 2A:
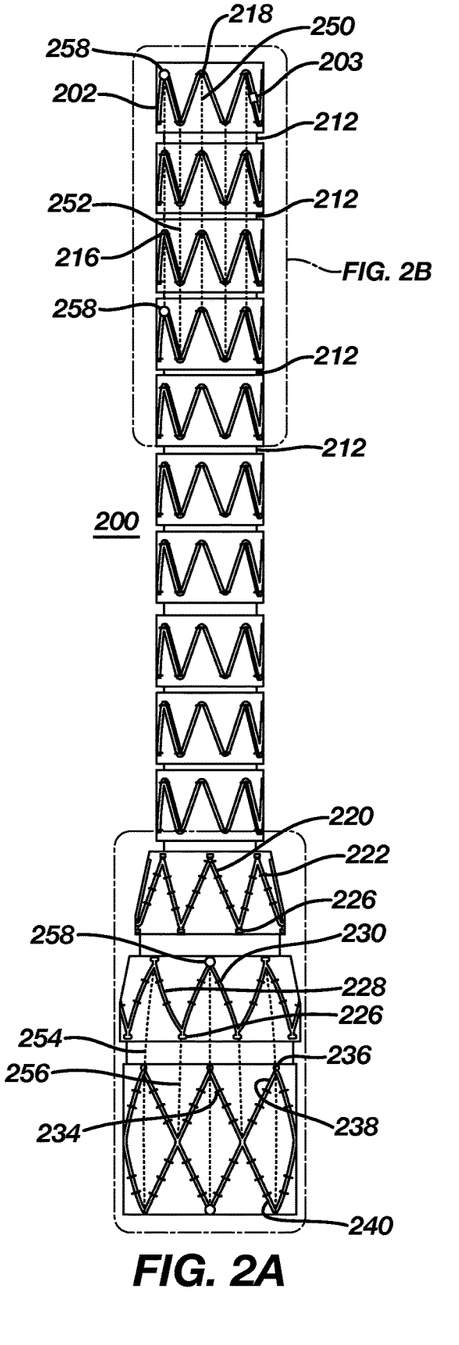
FIG. 2A is a diagrammatic representation of an extension that can be used with a leg of the main body.

Referring now to FIG. 2A, there is illustrated an exemplary embodiment of an endovascular graft extension 200 of the aneurysm repair device. The exemplary endovascular graft extension 200 may include one or more first stent hoops 202, a second stent hoop 204, a third stent hoop 206 and a fourth stent hoop 208. Graft material 210 is attached to the stent hoops 202, 204, 206 and 208 to form a substantially tubular conduit. As in the above described design, crimped sections 212 are formed in the graft material 210 between the stent hoops to increase flexibility. In a typical use scenario, the fourth stent hoop 208 would be anchored in healthy tissue below the aneurysm and a number of the uppermost first stent hoops 202 would overlap with one of the legs 106 and 108 of the anchoring and sealing component 100 thereby establishing a fluid channel through the diseased section of the artery. The degree of overlap may vary. Obviously the greater the degree of overlap, the less likely the chance of separation. In addition, as is explained in detail subsequently, the endoprosthesis suture locks of the present invention have more chances to engage with a higher degree of overlap. In this exemplary embodiment, a second endovascular graft would be connected to the second leg. As stated above, additional endovascular grafts may be connected together if longer conduits are required to bypass the diseased tissue.

The one or more first stent hoops 202 each may include a single row of struts 214 arranged in a substantially zigzag configuration. Sutures 216 are utilized to secure the graft material 210 to the stent hoops 202. These sutures 216 are only utilized to secure the graft material 210 proximate the apexes 218 of the first stent hoops 202 rather than along the entire length of a strut forming the segment 202. The diameter of the one or more first stent hoops 202 with the graft material 210 attached thereto is substantially equal to that of either of the legs 106 and 108 such that a tight interference fit may be achieved when the components are attached. In the exemplary embodiment, the endovascular graft extension 200 fits inside of the legs 106 and 108; however, in alternate exemplary embodiments wherein the endovascular graft extension 200 fits over or outside of the legs 106 and 108. As described in detail below, knots on the sutures of the cranial or cranial end of the endovascular graft extension 200 help anchor the endovascular graft within the legs 106 and 108.

The upper or caudal most first stent hoop 202 may include a marker band 203 for positioning the device. Once again, the marker band 203 may include any suitable, highly radiopaque material such as tantalum. It is worthwhile to note that while a number of different markers are illustrated, additional markers that are not shown are positioned at various locations around each of the components so that the physician may easily visualize the device under radio fluoroscopy.

The second segment 204 may include a single row of struts 220 arranged in a substantially zigzag configuration. The diameter of the stent hoop 204 is slightly larger than the diameter of the stent hoop 202. The increase in diameter may be achieved through the use of longer struts. Sutures 222 are utilized to secure the graft material 210 to the stent hoop 204. These sutures 222 are only utilized to secure the graft material 210 proximate the apexes 224 of the second stent hoop 204 rather than along the entire length of a strut forming the segment 204. In addition, each stent hoop 204 may include a suture locking mechanism 226 on at least one upper and lower apex 224. These suture locking mechanisms 226 allow for special suture knots to secure the graft material 210 to the stent hoop 204. It has been determined that these locations are subject to wear due to high biological forces and thus additional securing mechanism are utilized to prevent separation of the graft material 210.

Third stent hoop 206 is identical to stent hoop 204 with one exception. Specifically, the struts 228 forming this third stent hoop 206 are tapered outward in the circumferential direction thereby causing the diameter of the lower portion of the endovascular graft extension 200 to increase where it anchors in the vessel. Sutures 230 are utilized to secure the graft material 210 to the third sent segment 206. As with the second stent hoop 204, third stent hoop 206 also may include suture locking mechanisms 226 on at least one upper and lower apex 224. The diameter of the third stent hoop 206 is substantially equal to the diameter of the second stent hoop 204 on one end and substantially equal to the diameter of the fourth stent hoop 208 on the other end.

The fourth stent hoop 208 has a diamond shaped configuration formed from a plurality of struts 232. Sutures 234 are utilized to secure the graft material 210 to the fourth stent hoop 208. Suture locking mechanisms 236 are utilized on one or more apexes 238 only on the end of the fourth stent hoop 208 proximate the third stent hoop 206. The fourth stent hoop 208 also may include at least one marker band 240 attached to a strut for imaging the device. As described above, the marker band 240 may include any suitable, highly radiopaque material such as tantalum.

Thus, as described above and shown in FIGS. 2A and 2B, a first tubular extension 200 is configured for insertion into one of the two legs 106 and 108 of the main body 102 and a second tubular extension 200 is configured for its insertion into the other of the two legs. It is noted that each of the first and second tubular extensions 200 has an outer surface and an inner surface. The inner surface of graft 200 preferably has the stent hoops mounted on such surface while the outside surface of the graft 200 preferably has a retention mechanism provided thereon. Details of the graft retention mechanism to improve the retainability of the caudal or cranial end of the graft to the leg 106 or 108 are shown further in the enlarged FIG. 2B. Details of the mechanism to improve the retainability of the cranial or caudal end to the blood vessel are shown in the enlarged FIG. 2D.

Figure 2B:
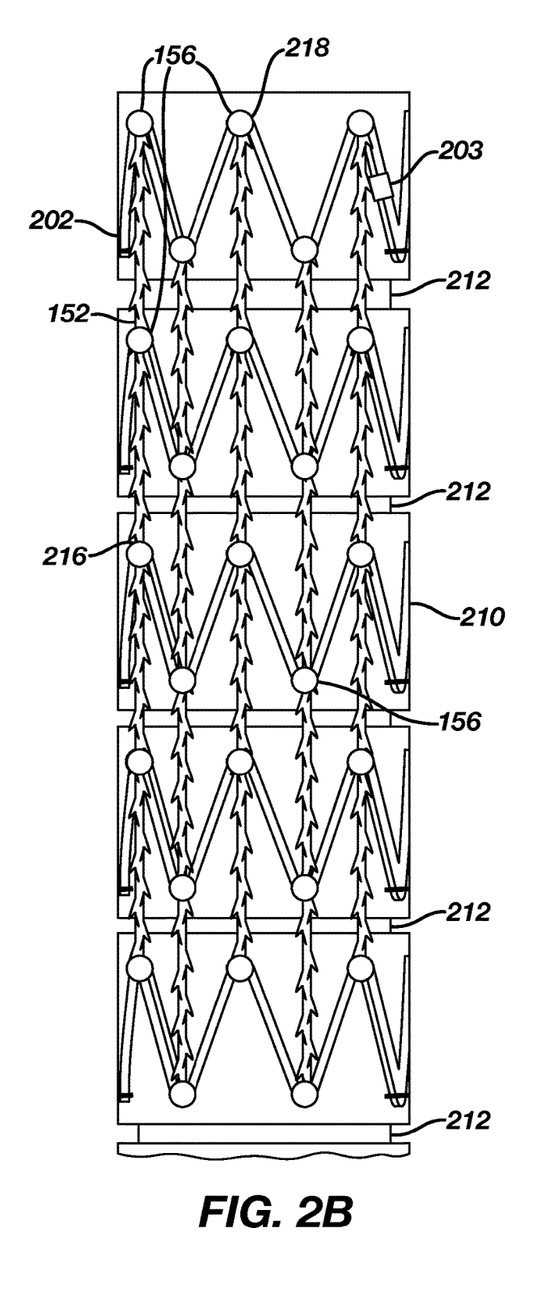
FIG. 2B is a close up view of a caudal end of the extension that can be used for insertion into one of the legs of the main body.
Figure 2C:
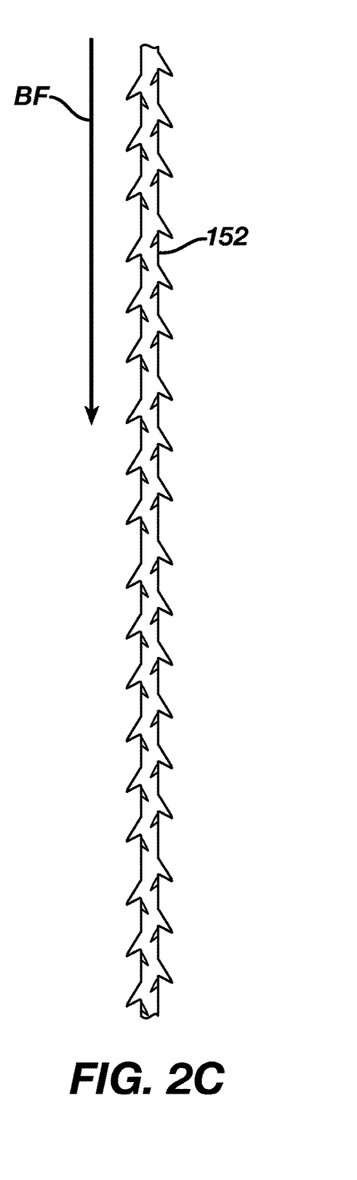
FIG. 2C is a close up view of a configuration of the suture utilized in the cranial portion of the extension of FIG. 2B.

In FIG. 2B, suture knots 156 can be used at various suitable locations to retain the barbed sutures 152 (shown in greater detail in FIG. 2C) to the graft 200. For example, the barbed suture 152 may be aligned with the apices of the stent hoops and secured proximate the apices as the suture 152 extends along the length of the graft. Alternatively, certain apices may be skipped as shown on the far right side of the graft. The barbs are oriented to resist against the force of the blood flow (BF) impinging on the graft 200. Due to the pulsing nature of blood flow, the barbs can be configured to resist both the blood flow and any resulting back flow by having barbs oriented in opposed directions.

Figure 2D:
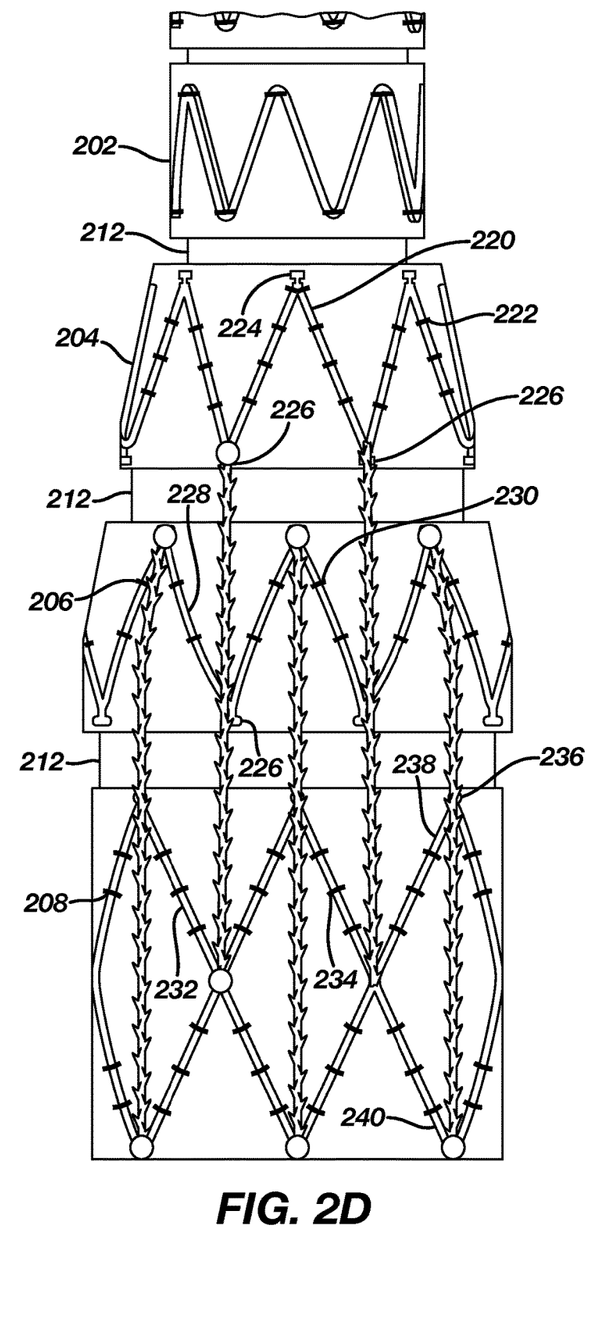
FIG. 2D is a close-up view of the cranial end of the extension in FIG. 2A that is configured to remain in place in the arterial vessel after deployment.
Figure 2E:
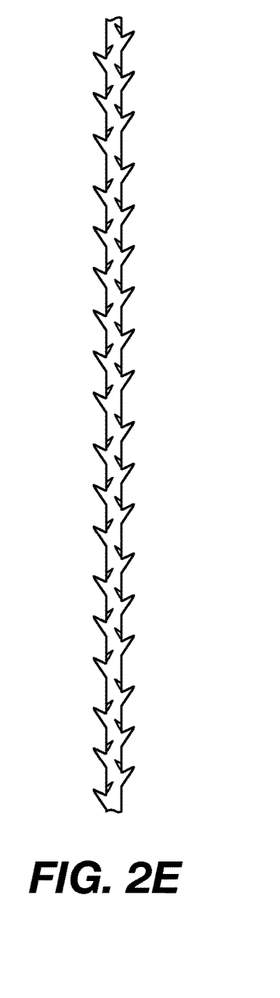
FIG. 2E is a close-up view of another configuration of the suture utilized in the caudal portion of the extension in FIG. 2D.

In FIG. 2D, sutures 152 can also be utilized to secure the caudal portion of graft 200 to respective blood vessels after bifurcation of the abdominal artery. Sutures 152, however, are preferably arranged, in FIG. 2E, such that the caudal portion can resist the force due to backflow of blood due to the pulsatile nature of blood flowing from the main artery. Nevertheless, the barbed sutures can be configured to resist both the blood flow and any resulting back flow by having barbs oriented in opposed directions.

The sutures 152 or 154 can be infused or loaded with bioactive agents to aid in the healing response or to achieve a desired physiological response. For example, bio-active agents such as blood de-clotting agent (e.g., heparin, warfarin, etc.,) anti-proliferative/antimitotic agents including natural products such as *vinca* alkaloids (i.e. vinblastine, vincristine, and vinorelbine), paclitaxel, epidipodophyllotoxins (i.e. etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagine); antiplatelet agents such as G(GP) IIb/IIIa inhibitors and vitronectin receptor antagonists; anti-proliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nirtosoureas (carmustine (BCNU) and analogs, streptozocin), trazenes-dacarbazinine (DTIC); anti-proliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine {cladribine}); platinum coordination complexes (cisplatin, carboplatin), procarbazine, hydroxyurea, mitotane, aminoglutethimide; hormones (i.e. estrogen); anti-coagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory; antisecretory (breveldin); anti-inflammatory: such as adrenocortical steroids (cortisol, cortisone, fludrocortisone, prednisone, prednisolone, 6α-methylprednisolone, triamcinolone, betamethasone, and dexamethasone), non-steroidal agents (salicylic acid derivatives i.e. aspirin; para-aminophenol derivatives i.e. acetominophen; indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressives: (cyclosporine, tacrolimus (FK-506), sirolimus (rapamycin), azathioprine, mycophenolate mofetil); angiogenic agents: vascular endothelial growth factor (VEGF), fibroblast growth factor (FGF); angiotensin receptor blockers; nitric oxide donors; anti-sense oligionucleotides and combinations thereof; cell cycle inhibitors, mTOR inhibitors, and growth factor receptor signal transduction kinase inhibitors; retenoids; cyclin/CDK inhibitors; HMG co-enzyme reductase inhibitors (statins); and protease inhibitors.

All of the stent hoops described herein are substantially tubular elements that may be formed utilizing any number of techniques and any number of materials. In the preferred exemplary embodiment, all of the stent hoops are formed from a nickel-titanium alloy (Nitinol), shape set laser cut tubing.

The graft material utilized to cover all of the stent hoops may be made from any number of suitable biocompatible materials, including woven, knitted, sutured, extruded, or cast materials forming polyester, polytetrafluoroethylene, silicones, urethanes, and ultra-light weight polyethylene, such as that commercially available under the trade designation SPECTRA™. The materials may be porous or non-porous. Exemplary materials include a woven polyester fabric made from DACRON™ or other suitable PET-type polymers.

In one exemplary embodiment, the fabric for the graft material is a forty denier (denier is defined in grams of nine thousand meters of a filament or yarn), twenty-seven filament polyester yarn, having about seventy to one-hundred end yarns per cm per face and thirty-two to forty-six pick yarns per cm face. At this weave density, the graft material is relatively impermeable to blood flow through the wall, but is relatively thin, ranging between 0.08 and 0.12 mm in wall thickness.

Prior to attachment of the graft component to the stent hoops, crimps are formed between the stent positions by placing the graft material on a shaped mandrel and thermally forming indentations in the surface. In the exemplary embodiment illustrated in FIGS. 1 and 2, the crimps 146 and 212 respectively, are about two mm long and 0.5 mm deep. With these dimensions, the endovascular graft can bend and flex while maintaining an open lumen. Also, prior to attachment of the graft material to the stent hoops, the graft material is cut in a shape to conform to the shapes of the stent hoops.

As stated above, the graft material is attached to each of the stent hoops. The graft material may be attached to the stent hoops in any number of suitable ways. In the exemplary embodiment, the graft material is attached to the stent hoops by sutures.

Figure 3:
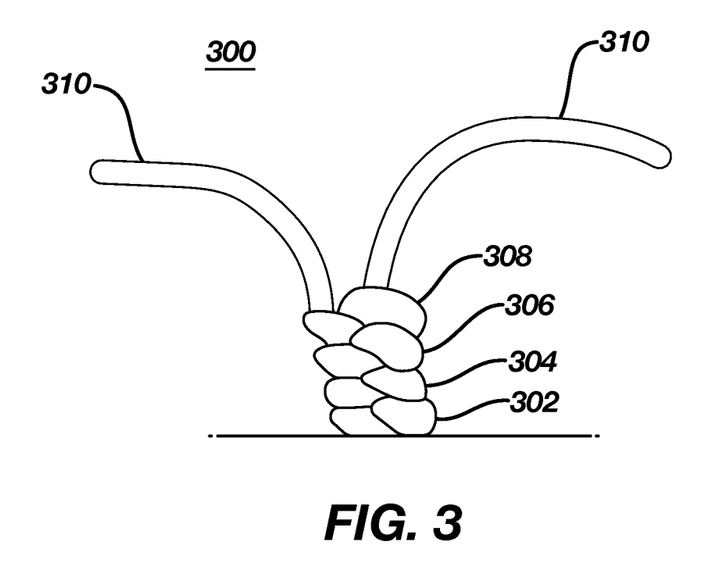
FIG. 3 is a diagrammatic representation of a first exemplary four-point suture knot in accordance with the present invention.
Figure 4A:
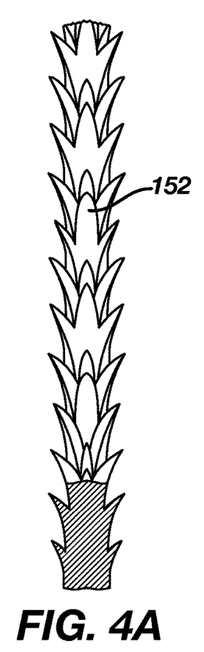
FIGS. 4A-4I illustrate the various configurations of the directional sutures that can be utilized as part of various embodiments of the invention.
Figure 4B:
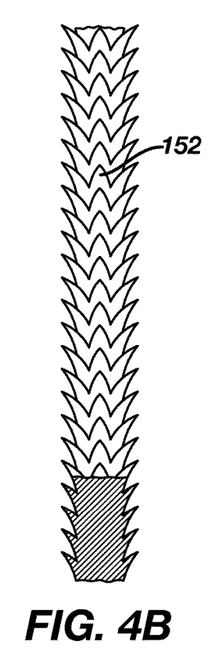
Figure 4C:
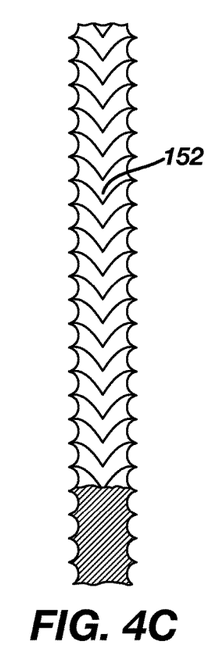
Figure 4D:
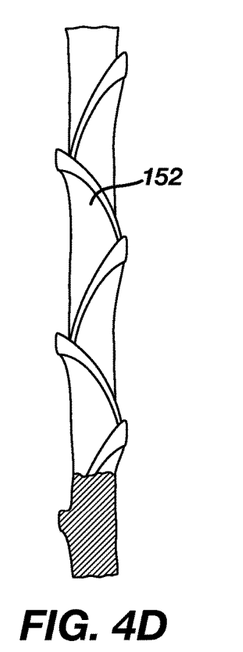
Figure 4E:
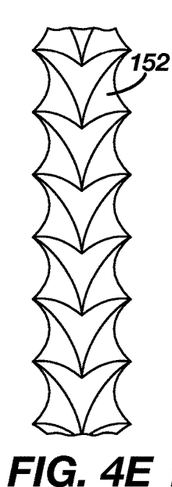
Figure 4F:
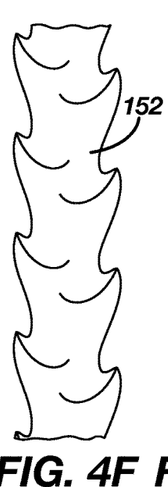
Figure 4G:
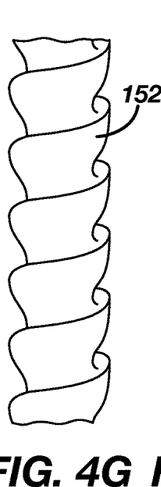
Figure 4H:
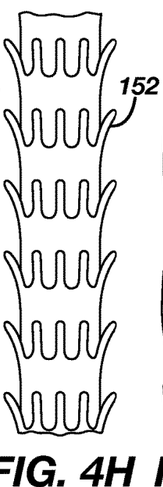
Figure 4I:
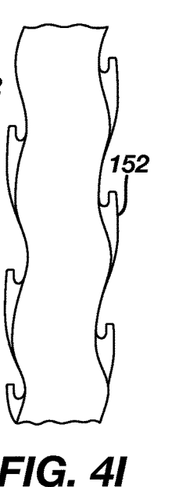

Depending on the stent hoops location, different types of sutures may be utilized. In the exemplary embodiment illustrated in FIG. 1B, in the lower portion of the first stent hoop 112, the graft material 110 with sutures 121 using a blanket type stitch. For stent hoops 122, 124 and 126, the graft material is attached with sutures 130 using a blanket type stitch. For the stents segments 136, the graft material is attached with sutures 140 using point type stitches. In the exemplary embodiment illustrated in FIG. 2A, the graft material 210 is attached to first stent hoops by sutures 216 using point type stitches. For stent hoop 204, the graft material 210 is attached using sutures 222 using blanket type stitches. For stent hoop 206, the graft material 210 is attached using sutures 230 using blanket type stitches. For stent element 208, the graft material 210 is attached using sutures 234 using blanket type stitches, shown here in FIG. 3. Additionally, the suture knots utilized to fasten the graft material to the underlying stent structures may be modified to enhance the overall performance of the aneurysm repair device. Essentially, the modified suture knots may be utilized to create tailored profiles that increase the ability of one component to adhere the other components and/or vessels to prevent component separation or migration. Details of various embodiments of the suture knots can be found in US Patent Application Publication No. US20110071614 filed on Sep. 24, 2009, which is hereby incorporated by reference as if set forth herein.

Although two configurations have been shown for barbed suture 150, 152, or 154, it is within the scope of this disclosure to also utilize variations of the barbs such as those shown, for example, in FIGS. 4A-4I, which can be in the form of undulations or ripples molded or formed in the suture. The suture may have a nominal diameter of about 0.1 millimeters to about 0.4 millimeters in short-term absorbable, long-term absorbable and nonabsorbable polymer configurations. It should also be noted that while the barbs are shown in the plan view in two-dimension, in actual use, the barbs are configured such that the actual barbs would also extend to contact the vessel (e.g., FIG. 2B) in which the endoprosthesis is deployed. In other words, a viewer of the barbs placed on the plan views of the figures would have the barbs extending towards the viewers (i.e., projecting out of the drawings) so that at least a portion of the barbs would contact the vessel in which the endoprosthesis is deployed.

While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well.

What is claimed is:

1. An endoprosthesis for repair of aneurysm in an artery that has an arterial bifurcation for blood to flow downstream from the artery to the bifurcation, the endoprosthesis comprising:
  a main body configured to be placed in an artery upstream of the arterial bifurcation, the main body having a distal end with an anchor portion connected to a fabric portion of the main body, the fabric having inner and outer surfaces, the fabric portion being connected to a first plurality of spaced apart stent hoops, the main body extending from the distal end along a longitudinal axis into two tubular flow passages or legs, wherein each of the legs includes its own longitudinal axis as well as respective second and third plurality of spaced apart stent hoops connected to the fabric portion of each leg;
  a first tubular extension configured for insertion into one of the two legs;
  a second tubular extension configured for insertion into the other of the two legs, each of the first and second tubular extensions having an outer surface and an inner surface; and
  at least a first suture disposed along on the outer surface of the main body, the at least a first suture connects at least two of the spaced apart stent hoops on the main body together, the at least a first suture including unidirectional barbs configured to reduce movement of the main body with respect to the artery in the direction of blood flow.

2. The endoprosthesis of claim 1, in which the at least a first suture comprises a plurality of sutures connected to the anchor portion and at least two spaced apart stent hoops.

3. The endoprosthesis of claim 1, in which the at least a first suture comprise a plurality of sutures connected to an apex of one stent hoop to an apex of another stent hoop.

4. The endoprosthesis of claim 1, in which the at least a first suture comprises a bioresorbable material.

5. The endoprosthesis of claim 1, in which the at least a first suture comprises a non-bioresorbable material.

6. The endoprosthesis of claim 1, in which the at least a first suture comprises a shape memory material.

7. The endoprosthesis of claim 1, further comprising suture knots extending through the graft portion to secure the at least a first suture to the graft portion and the stent hoop.

8. The endoprosthesis of claim 7, in which the knots are located proximate respective apices that are defined by a sinusoidal structure of the stent hoop.

9. The endoprosthesis of claim 1, wherein the spaced apart stent hoops are disposed on the inner surface of the graft portion.

10. The endoprosthesis of claim 1, further comprising at least a second suture disposed along the outer surface of a distal end of at least one of the tubular extensions so that unidirectional barbs disposed on the at least second suture prevents movement of the at least one tubular extension relative to the respective legs of the main body.

11. The endoprosthesis of claim 1, further comprising at least a third suture disposed along the outer surface of a proximal end of at least one of the tubular extensions so that unidirectional barbs disposed on the at least second suture.

12. The endoprosthesis of claim 1, further comprising at least a fourth suture disposed about the circumference of the outer surface of the graft material proximate a junction between the anchor portion and the graft portion of the main body, the at least a fourth suture comprising a section having barbs oriented in a first direction and another section having barbs oriented in a second direction generally opposite the first direction.

13. The endoprosthesis of claim 1, in which the first suture includes a bioactive agent dispersed in the first suture to aid in a healing response.

14. The endoprosthesis of claim 1, in which the barbs include a continuous helical protrusion.

15. The endoprosthesis of claim 1, in which the barbs include projections extending away from the suture.

16. The endoprosthesis of claim 1, in which the barbs include projections extending away from the suture at an angle relative to the suture.

17. The endoprosthesis of claim 1, in which the barbs include undulations formed as part of the suture.

18. The endoprosthesis of claim 1, in which the barbs are configured to extend away from the longitudinal axis so as to contact an inner surface of a tissue vessel in which the endoprosthesis is deployed therein.

* * * * *